(12) United States Patent
McBrady et al.

(10) Patent No.: US 11,878,086 B2
(45) Date of Patent: Jan. 23, 2024

(54) APPARATUSES AND METHODS FOR IMPROVED SANITIZATION

(71) Applicant: Honeywell International Inc., Morris Plains, NJ (US)

(72) Inventors: Adam Dewey McBrady, Dallas, TX (US); Moin S. Shafai, Plano, TX (US); Stephan Bork, Murphy, TX (US); Amrita G. Khemchandani, Tempe, AZ (US)

(73) Assignee: Honeywell International Inc., Morris Plains, NJ (US)

( * ) Notice: Subject to any disclaimer, the term of this patent is extended or adjusted under 35 U.S.C. 154(b) by 340 days.

(21) Appl. No.: 16/849,499

(22) Filed: Apr. 15, 2020

(65) Prior Publication Data

US 2021/0322616 A1 Oct. 21, 2021

(51) Int. Cl.
*A61L 2/28* (2006.01)
*G06T 7/73* (2017.01)
*A61L 2/10* (2006.01)
*G06T 15/20* (2011.01)

(52) U.S. Cl.
CPC .................. *A61L 2/28* (2013.01); *A61L 2/10* (2013.01); *G06T 7/74* (2017.01); *G06T 15/205* (2013.01)

(58) Field of Classification Search
CPC .......... A61L 2/28; A61L 2/10; A61L 2202/14; A61L 2/24; G06T 7/74; G06T 15/205; G06T 15/005; G06T 17/00; A61C 8/0087; A61C 19/002
See application file for complete search history.

(56) References Cited

U.S. PATENT DOCUMENTS

| | | | |
|---|---|---|---|
| 10,816,939 B1* | 10/2020 | Coleman | G01S 17/86 |
| 2016/0089457 A1 | 3/2016 | Liao et al. | |
| 2016/0361150 A1 | 12/2016 | Berndt et al. | |
| 2018/0061120 A1 | 3/2018 | Short et al. | |

(Continued)

FOREIGN PATENT DOCUMENTS

| | | |
|---|---|---|
| CN | 107690303 A | 2/2018 |
| CN | 107823678 A | 3/2018 |

(Continued)

OTHER PUBLICATIONS

Extended European search report dated Oct. 7, 2021 for EP Application No. 21166798, 7 pages.

(Continued)

*Primary Examiner* — Chong Wu
(74) *Attorney, Agent, or Firm* — Alston & Bird LLP (57) ABSTRACT

Methods, apparatuses, devices, and computer program products are disclosed for improved sanitization. An example device includes a sanitizing element that outputs a sanitizing agent. The device also includes a scanning device that generates scanning data of the physical form of the object. The device further includes a controller operatively coupled to the sanitizing element and the scanning device. The controller determines the output of the sanitizing agent during operation of the scanning device, receives the scanning data generated by the scanning device, and determines one or more areas of the object failing to receive sufficient contact with the sanitizing agent based upon the scanning data and sanitizing agent output.

17 Claims, 5 Drawing Sheets

(56) References Cited

U.S. PATENT DOCUMENTS

| | | |
|---|---|---|
| 2018/0071414 A1 | 3/2018 | Dujowich et al. |
| 2020/0101183 A1 | 4/2020 | Dijkstra et al. |

FOREIGN PATENT DOCUMENTS

| | | |
|---|---|---|
| JP | 2018-197128 A | 12/2018 |
| KR | 10-2020-0031866 A | 3/2020 |
| WO | 2015/116876 A1 | 8/2015 |
| WO | 2015/116982 A1 | 8/2015 |

OTHER PUBLICATIONS

3Shape TRIOS® Intraoral Scanner—Explore the Scanners & Software [online] [retrieved May 21, 2020]. Retrieved from the Internet: htttps://www.3shape.com/en/scanners/trios, 19 pages.

HandyScan 3D Professional Metrology-Grade 3D Scanners [online] [retrieved May 21, 2020]. Retrieved from the Internet: https://www.creaform3d.com/en/portable-3d-scanner-handyscan-3d (Undated) 8 pages.

CN Office Action, including Search Report, dated Oct. 9, 2022 for CN Application No. 202110291821, 12 pages.

English Translation of CN Office Action, including Search Report, dated Oct. 9, 2022 for CN Application No. 202110291821, 12 pages.

CN Office Action dated Apr. 22, 2023 for CN Application No. 202110291821, 8 page(s).

English Translation of CN Office Action dated Apr. 22, 2023 for CN Application No. 202110291821, 7 page(s).

Communication about intention to grant a European patent dated Jan. 16, 2023 for EP Application No. 21166798.

Decision to grant a European patent dated May 25, 2023 for EP Application No. 21166798, 2 page(s).

CN Notice of Allowance dated Jun. 30, 2023 for CN Application No. 202110291821, 2 page(s).

English translation of CN Notice of Allowance dated Jun. 30, 2023 for CN Application No. 202110291821, 3 page(s).

\* cited by examiner

APPARATUSES AND METHODS FOR IMPROVED SANITIZATION

TECHNOLOGICAL FIELD

Example embodiments of the present disclosure relate generally to sanitization operations and, more particularly, to ensuring proper object disinfection.

BACKGROUND

Objects, surfaces, and the like may host viruses, bacteria, germs, and other harmful substances. In many instances, these microorganisms and substances may live on surfaces for extended periods of time and even small locations on these objects containing germs may pose a significant threat. Through applied effort, ingenuity, and innovation, many of the sanitization issues identified have been solved by developing solutions that are included in embodiments of the present disclosure, many examples of which are described in detail herein.

BRIEF SUMMARY

Systems, apparatuses, methods, and computer program products are disclosed herein for improved sanitization. With reference to an example device, the device may include a sanitizing element configured to output a sanitizing agent for disinfecting an object. The device may further include a scanning device configured to generate scanning data of the physical form of the object. The device may also include a controller operatively coupled to the sanitizing element and the scanning device. The controller may be configured to determine the output of the sanitizing agent during operation of the scanning device, receive the scanning data generated by the scanning device, and determine one or more areas of the object failing to receive sufficient contact with the sanitizing agent based upon the scanning data and sanitizing agent output.

In some embodiments, the sanitizing element is an ultraviolet (UV) light such that the sanitizing agent is UV electromagnetic radiation.

In some embodiments, the scanning device comprises a three dimensional (3D) scanner.

In some further embodiments, the device may include a housing supporting the sanitizing element and the scanning device. The housing may be configured to position the sanitizing element proximate to the scanning device such that a scanning direction of the scanning device substantially aligns with the output of the sanitizing agent.

In some embodiments, the controller may be further configured to generate an indication of the one or more areas of the object failing to receive sufficient contact with the sanitizing agent.

In some embodiments, the controller may be further configured to, in response to receiving the scanning data, generate a three dimensional (3D) rendering of the object. In such an embodiment, the controller may be further configured to generate an indication of the one or more areas of the object failing to receive sufficient contact with the sanitizing agent on the 3D rendering of the object.

In some further embodiments, the controller may be configured to analyze the scanning data to determine a position of the device relative to the object, receive an intensity distribution of the sanitizing agent at the position from the sanitizing element, and compare the intensity distribution with an exposure threshold. In an instance in which the intensity distribution fails to satisfy the exposure threshold, the controller may determine that the position corresponds to an area of the object failing to receive sufficient contact with the sanitizing agent.

In some further embodiments, the scanning data further may include associated time data.

In some other further embodiments, the controller may determine a valid condition in an instance in which the intensity distribution at each position of the object satisfies the exposure threshold.

In some embodiments, the controller may be further configured to store the determination of the valid condition for the object.

In other embodiments, the controller may be configured to modify the exposure threshold based upon one or more previous determinations of the valid condition.

The above summary is provided merely for purposes of summarizing some example embodiments to provide a basic understanding of some aspects of the disclosure. Accordingly, it will be appreciated that the above-described embodiments are merely examples and should not be construed to narrow the scope or spirit of the disclosure in any way. It will be appreciated that the scope of the disclosure encompasses many potential embodiments in addition to those here summarized, some of which will be further described below.

BRIEF DESCRIPTION OF THE DRAWINGS

Having described certain example embodiments of the present disclosure in general terms above, reference will now be made to the accompanying drawings. The components illustrated in the figures may or may not be present in certain embodiments described herein. Some embodiments may include fewer (or more) components than those shown in the figures.

DETAILED DESCRIPTION

Some embodiments of the present disclosure will now be described more fully hereinafter with reference to the accompanying drawings, in which some, but not all embodiments of the disclosure are shown. Indeed, this disclosure may be embodied in many different forms and should not be construed as limited to the embodiments set forth herein; rather, these embodiments are provided so that this disclosure will satisfy applicable legal requirements. Like numbers refer to like elements throughout. As used herein, the description may refer to a controller and device as an example "apparatus." However, elements of the apparatus described herein may be equally applicable to the claimed method and computer program product. Thus, use of any such terms should not be taken to limit the spirit and scope of embodiments of the present disclosure.

Definition of Terms

As used herein, the terms "data," "content," "information," "electronic information," "signal," "command," and similar terms may be used interchangeably to refer to data capable of being transmitted, received, and/or stored in accordance with embodiments of the present disclosure. Thus, use of any such terms should not be taken to limit the spirit or scope of embodiments of the present disclosure. Further, where a first computing device is described herein to receive data from a second computing device, it will be appreciated that the data may be received directly from the second computing device or may be received indirectly via one or more intermediary computing devices, such as, for example, one or more servers, relays, routers, network access points, base stations, hosts, and/or the like, sometimes referred to herein as a "network." Similarly, where a first computing device is described herein as sending data to a second computing device, it will be appreciated that the data may be sent directly to the second computing device or may be sent indirectly via one or more intermediary computing devices, such as, for example, one or more servers, remote servers, cloud-based servers (e.g., cloud utilities), relays, routers, network access points, base stations, hosts, and/or the like.

As used herein, the term "comprising" means including but not limited to and should be interpreted in the manner it is typically used in the patent context. Use of broader terms such as comprises, includes, and having should be understood to provide support for narrower terms such as consisting of, consisting essentially of, and comprised substantially of.

As used herein, the phrases "in one embodiment," "according to one embodiment," "in some embodiments," and the like generally refer to the fact that the particular feature, structure, or characteristic following the phrase may be included in at least one embodiment of the present disclosure. Thus, the particular feature, structure, or characteristic may be included in more than one embodiment of the present disclosure such that these phrases do not necessarily refer to the same embodiment.

As used herein, the word "example" is used herein to mean "serving as an example, instance, or illustration." Any implementation described herein as "example" is not necessarily to be construed as preferred or advantageous over other implementations.

As used herein, the term "computer-readable medium" refers to non-transitory storage hardware, non-transitory storage device or non-transitory computer system memory that may be accessed by a controller, a microcontroller, a computational system or a module of a computational system to encode thereon computer-executable instructions or software programs. A non-transitory "computer-readable medium" may be accessed by a computational system or a module of a computational system to retrieve and/or execute the computer-executable instructions or software programs encoded on the medium. Exemplary non-transitory computer-readable media may include, but are not limited to, one or more types of hardware memory, non-transitory tangible media (for example, one or more magnetic storage disks, one or more optical disks, one or more USB flash drives), computer system memory or random access memory (such as, DRAM, SRAM, EDO RAM), and the like.

Having set forth a series of definitions called-upon throughout this application, an example system architecture and example apparatus is described below for implementing example embodiments and features of the present disclosure.

Device for Improved Sanitization

As described above, objects, items, surfaces, and the like may host or otherwise support viruses, bacteria, germs, microorganisms and other harmful substances. In particular, hospital, school, and other similar environments may be at an increased risk for contamination and may look to disinfecting or sanitizing solutions to reduce the risk associated with these microorganisms. In many instances, these microorganisms may live on surfaces for extended periods of time and even small areas on these objects containing germs may pose a significant threat. Traditional cleaning has relied upon antibacterial or disinfectant wipes, ultraviolet (UV) applications, thermal applications, fogging agent applications, or the like to neutralize germ related threats. These traditional methods, however, fail to ensure that sanitization is effectively completed and often result in areas of objects and items that continue to host germs. Furthermore, many objects are repeatedly used, such as in hospital environments, and required to be sanitized after each use. The monitoring of these sanitizing operations, however, is cumbersome and often unverifiable.

To solve these issues and others, example implementations of embodiments of the present disclosure may utilize a sanitizing element that outputs a sanitizing agent in conjunction with a scanning device to ensure objects are properly disinfected. In operation, embodiments of the present disclosure may determine and/or monitor the output of sanitizing agent during operation of the scanning device and receive scanning data representative of the physical form of the object. These embodiments may further determine one or more areas of the object that fail to receive sufficient contact with the sanitizing agent and may output an indication to a user of these areas. In doing so, the embodiments of the present application may ensure that an objection is effectively disinfected and may further provide a verifiable record of sanitization operations.

Figure 1:
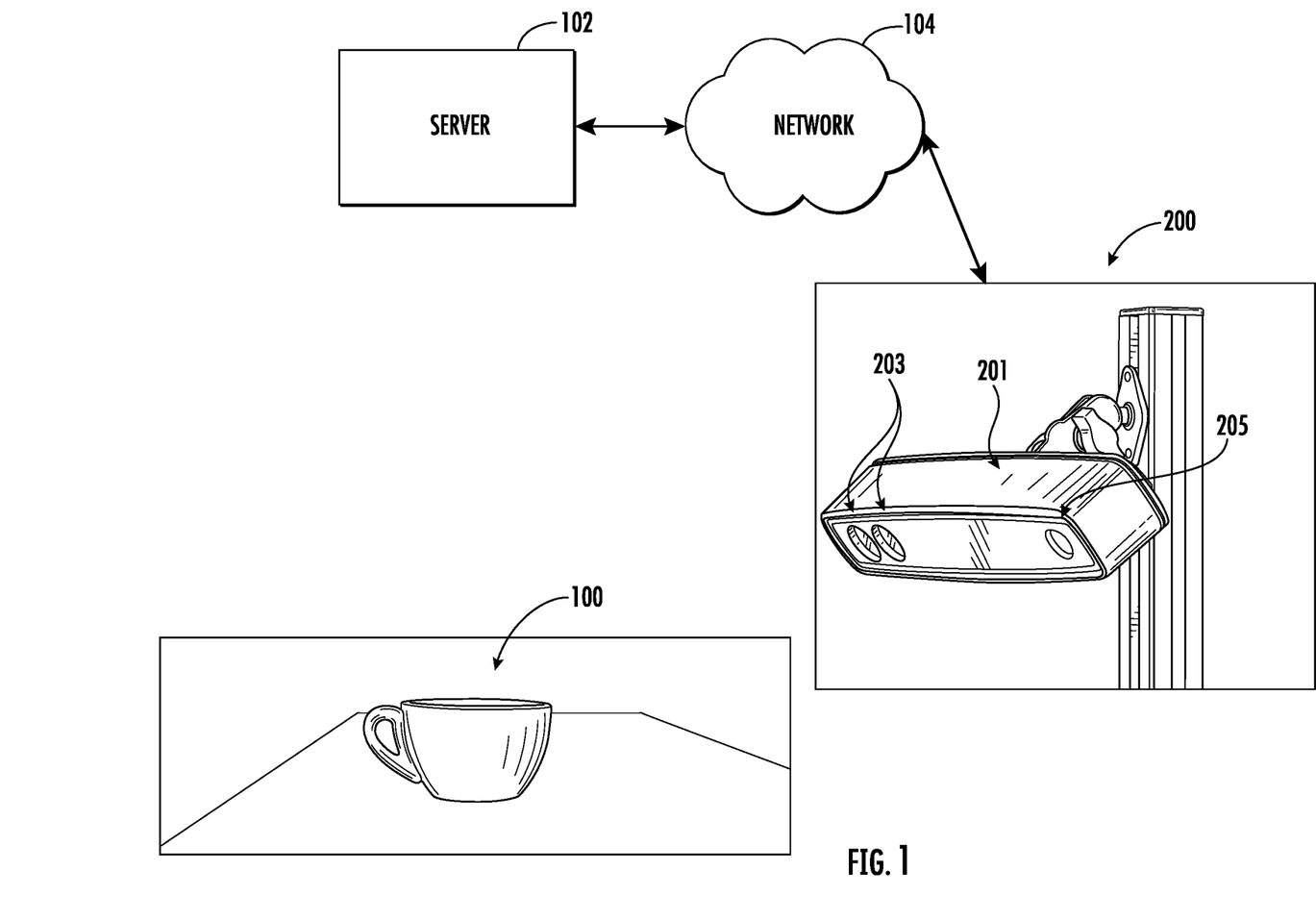
FIG. 1 illustrates a device for improved sanitization, in accordance with some example embodiments described herein.

With reference to FIG. 1, an example device 200 (e.g., device for improved sanitization) is illustrated communicably connected via a network 104 to a sever 102. As shown, the device 200 may also include a sanitizing element 205 and a scanning device 203 supported by a housing 201. The device 200, in operation, may be configured to analyze and disinfect/sanitize an object 100 via the scanning device 203 and sanitizing element 205, respectively.

As shown, the device 200 may be communicably coupled with the server 102 (e.g., cloud-based server or otherwise) such that the device 200 may transmit data to and receive data from the server 102. By way of example, the device 200 may be configured to output data to the server 102 over the network 104 regarding the sanitizing of the object 100. The server 102 may include circuitry, networked processors, or the like configured to perform various processes described herein, in whole or in part, and may be any suitable network server and/or other type of processing device. In this regard, the server 102 may be embodied by any of a variety of devices. For example, the server 102 may be configured to receive/transmit data and may include any of a variety of fixed terminals, such as a server, desktop, or kiosk, or it may comprise any of a variety of mobile terminals, such as a portable digital assistant (PDA), mobile telephone, smartphone, laptop computer, tablet computer, or in some embodiments, a peripheral device that connects to one or more fixed or mobile terminals. In some embodiments, the server 102 may be located remotely from device 200. The server 102 may, in some embodiments, comprise several servers or computing devices performing interconnected and/or distributed functions. Said differently, in some embodiments the server 102 may be configured as a locally-hosted server, a cloud-based, distributed server, or a peer-to-peer network. Despite the many arrangements contemplated herein, the server 102 is shown and described herein as a single computing device to avoid unnecessarily over-complicating the disclosure.

The network 104 may include one or more wired and/or wireless communication networks including, for example, a wired or wireless local area network (LAN), personal area network (PAN), metropolitan area network (MAN), wide area network (WAN), or the like, as well as any hardware, software and/or firmware for implementing the one or more networks (e.g., network routers, switches, hubs, etc.). For example, the network 104 may include a cellular telephone, mobile broadband, long term evolution (LTE), GSM/EDGE, UMTS/HSPA, IEEE 802.11, IEEE 802.16, IEEE 802.20, Wi-Fi, dial-up, 3G, 4G, 5G, and/or WiMAX network. Furthermore, the network 104 may include a public network, such as the Internet, a private network, such as an intranet, or combinations thereof, and may utilize a variety of networking protocols now available or later developed including, but not limited to TCP/IP based networking protocols.

The object 100 may refer to any item, surface, element, feature, component, area, face, side, etc. that may be disinfected or sanitized by the device 200. As shown, the object 100 may be, for example, a cup that may host or otherwise support microorganisms as described above. Although illustrated and described herein with reference to a cup, the present disclosure contemplates that the object 100 may be any item without limitation. Furthermore, the present disclosure contemplates that the object 100 may include any number of surfaces, nooks, crevices, cavities, openings, or the like such that, as the number of features defined by the object 100 increases, the associated sanitization of the object 100 also increases in difficultly. Said differently, sanitizing or disinfecting an object 100 having a simple geometric shape (e.g., a flat surface, table, or the like) may require less time and/or sanitizing agent as compared to an object 100 having a complex geometric shape.

With continued reference to FIG. 1, the device 200 may include the sanitizing element 205 configured to output a sanitizing agent for disinfecting the object 100. By way of example the sanitizing element 205 may, in some embodiments, be an ultraviolet (UV) light. In such an embodiment, the sanitizing agent output by the sanitizing element 205 may be UV electromagnetic radiation. As such, the sanitizing element 205 may include one or more UV lights, lamps, light emitting diodes (LEDs) or the like configured to output UV electromagnetic radiation (ultraviolet germicidal irradiation) configured to neutralize germs, virus, bacteria, microorganisms, or the like located on the object 100. As would be evident by one of ordinary skill in the art in light of the present disclosure, the sanitizing element 205 may be configured to output UV electromagnetic radiation (e.g., the sanitizing agent) having an appropriate wavelength to kill or inactivate germs, viruses, bacteria, and/or other microorganisms. Furthermore, although illustrated with a single sanitizing element 205, the present disclosure contemplates that the sanitizing element 205 may include any number of UV lights, lamps, LEDs, or the like based upon the intended application of the device 200. Said differently, the sanitizing element 205 may be configured to produce a variable output of UV electromagnetic radiation based upon the object 100 to be disinfected, regulations or guidelines related to disinfecting of the object 100, and/or the like. The sanitizing element 205 may be powered by a power source or battery of the device 200 (not shown) or via electrical connection with an external power source.

Although described herein with reference to a disinfecting or sanitizing operation, the present disclosure contemplates that the device 200 may similarly be configured for use with resin curing implementations. The sanitizing element 205 may include one or more UV lights, lamps, light emitting diodes (LEDs) or the like configured to output UV electromagnetic radiation (ultraviolet germicidal irradiation) configured to cure resins applied to the object 100. By way of example, the object 100 may refer to a dental implant, a user's tooth, or the like that may receive a resin (or equivalent polymer) to, for example, fill an opening in the user's tooth. As such, the sanitizing element 205 may output a sanitizing agent (e.g., UV light) at an appropriate wavelength to cure the resin applied to the object. Although described with reference to a dental applications, the present disclosure contemplates that the device 200 may be used with any application in which resins or associated polymers are cured.

Although described herein with reference to the sanitizing element 205 including a UV lamp, the present disclosure contemplates that any form of optical radiation, x-ray, electron flux, or the like may be similarly used to output a corresponding sanitizing agent in order to disinfect the object 100. Furthermore, the present disclosure contemplates that any method of disinfecting the object 100 may also be used (e.g., non-radiation based methods). By way of example the sanitizing element 205 may, in some embodiments, include a fluid disinfectant applicator, aerosol spray, fogging chemical agent, or the like such that the sanitizing agent instead includes an antibacterial or otherwise disinfectant fluid. As described hereafter, the scanning device 203 may be similarly adapted for use with a fluid disinfectant application. In other embodiments, the sanitizing element 205 may include a thermal application (e.g., heat related sanitization) such that the sanitizing agent is heat. Similarly, in such an embodiment, the scanning device 203 may be adapted for use with a thermal application (e.g., a thermal or infrared camera).

With continued reference to FIG. 1, the device 200 may further include the scanning device 203 configured to generate scanning data. As described hereafter, the scanning data may be representative or otherwise indicative of the physical form (e.g., shape) of the object 100. By way of example, the scanning device 203 may include a three dimensional (3D) scanner configured to collect 3D data (e.g., scanning data) and generate a 3D model or rendering based upon the 3D data (e.g., scanning data). The scanning device 203 may include one or more optical engines, 3D tomographic sensors, cameras, 3D cameras, visible light sensors, laser tracker, or the like configured to generate 3D data (e.g., scanning data) representative of the physical form of the object 100. Although illustrated with two (2) 3D scanning devices, the present disclosure contemplates that the scanning device 203 may include any number of optical engines, 3D tomographic sensors, cameras, 3D cameras, visible light sensors, laser trackers, or the like based upon the intended application of the device 200. Furthermore, the present disclosure contemplates that the scanning device 203 may be configured to perform any 3D imaging technique including time-of-flight, triangulation, conoscopic holography, structured light, modulated light, volumetric, and/or any contact, non-contact active, or non-contact passive technique. The scanning device 203 may also be powered by a power source or battery of the device 200 (not shown) or via electrical connection with an external power source.

The device 200 may further include a housing 201 supporting the sanitizing element 205 and the scanning device 203. The housing 201 may be dimensioned (e.g., sized and shaped) to accommodate any number of elements of the sanitizing device 205 (e.g., UV lamps or the like) and any number of elements of the scanning device 203 (e.g., 3D cameras or the like). Furthermore, the housing 201 may be, in some embodiments, formed for use with a user's hand. Said differently, the housing 201 may be dimensioned (e.g., sized and shaped) to provide an ergonomic handle, form factor, etc. to be engaged by a user. In some embodiments, the housing 201 may position the sanitizing element 205 proximate to the scanning device 203 such that a scanning direction of the scanning device 203 substantially aligns with the output of the sanitizing agent. As described hereafter with reference to the operations of FIGS. 3-4, the device 200 may determine the output of sanitizing agent (e.g., outputted UV electromagnetic radiation) during operation of the scanning device 203. As such, the sanitizing device 205 may, in such an embodiment, be positioned in close proximity to the scanning device 203 such that the output direction (e.g., the cone of emitted UV electromagnetic radiation) substantially aligns (e.g., within applicable industry tolerances) with the field of view or scanning direction of the scanning device 203.

The device 200 may further include a controller (e.g., controller of FIG. 2) operatively coupled to the sanitizing element 205 and the scanning device 203. As described hereafter, the controller may include various circuitry components configured to, in some embodiments, control operation of the sanitizing element 205 and/or the scanning device 203. In other embodiments, the sanitizing element 205 and/or the scanning device 203 may include separate controllers, computing devices, or the like configured to, in whole or in part, control operation of the functions of these respective elements. In some still further embodiments, the server 102 may include various circuitry components configured to, in whole or in part, control operation of the device 200, the sanitizing element 205, and/or the scanning device 203. Example embodiments contemplated herein may have various form factors and designs but will nevertheless include at least the components illustrated in FIG. 2 and described in connection therewith.

Figure 2:
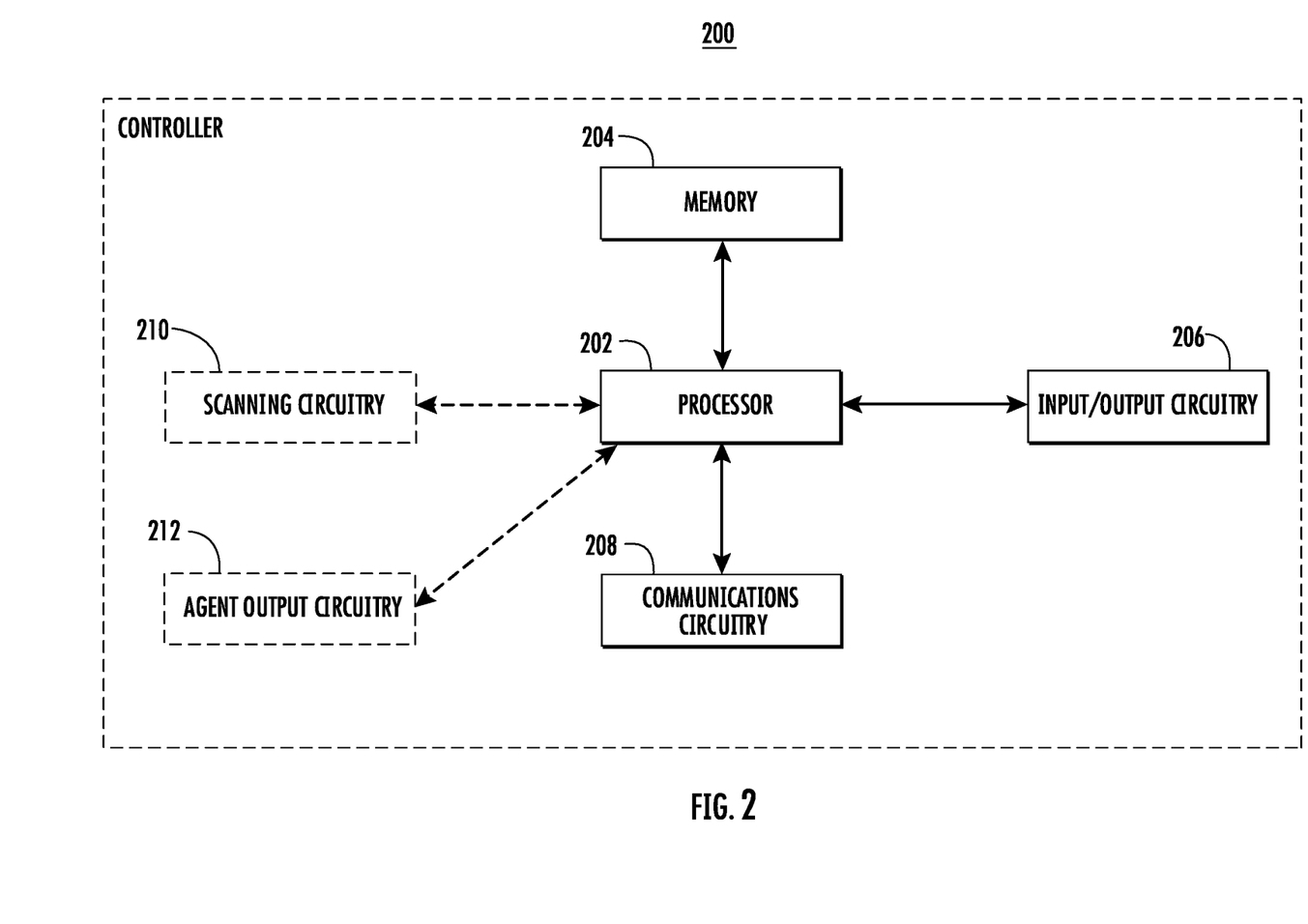
FIG. 2 illustrates a schematic block diagram of example circuitry that may perform various operations, in accordance with some example embodiments described herein.

As illustrated in FIG. 2, the device 200 may include a controller including a processor 202, a memory 204, communications circuitry 208, input/output circuitry 206, and, in some embodiments, scanning circuitry 210 and agent output circuitry 212. The controller may be configured to execute the operations described below in connection with FIGS. 3-4. Although components 202-212 are described in some cases using functional language, it should be understood that the particular implementations necessarily include the use of particular hardware. It should also be understood that certain of these components 202-212 may include similar or common hardware. For example, two sets of circuitry may both leverage use of the same processor 202, memory 204, communications circuitry 208, or the like to perform their associated functions, such that duplicate hardware is not required for each set of circuitry. The use of the term "circuitry" as used herein includes particular hardware configured to perform the functions associated with respective circuitry described herein. As described in the example above, in some embodiments, various elements or components of the circuitry of the controller may be housed within the sanitizing element 205, the scanning device 203, and/or the server 102. It will be understood in this regard that some of the components described in connection with the device 200 and associated controller may be housed within one of these devices, while other components are housed within another of these devices, or by yet another device not expressly illustrated in FIG. 1.

Of course, while the term "circuitry" should be understood broadly to include hardware, in some embodiments, the term "circuitry" may also include software for configuring the hardware. For example, although "circuitry" may include processing circuitry, storage media, network interfaces, input/output devices, and the like, other elements of the device 200 and controller may provide or supplement the functionality of particular circuitry.

In some embodiments, the processor 202 (and/or co-processor or any other processing circuitry assisting or otherwise associated with the processor) may be in communication with the memory 204 via a bus for passing information among components of the device 200. The memory 204 may be non-transitory and may include, for example, one or more volatile and/or non-volatile memories. In other words, for example, the memory may be an electronic storage device (e.g., a non-transitory computer readable storage medium). The memory 204 may be configured to store information, data, content, applications, instructions, or the like, for enabling the device 200 and controller to carry out various functions in accordance with example embodiments of the present disclosure.

The processor 202 may be embodied in a number of different ways and may, for example, include one or more processing devices configured to perform independently. Additionally, or alternatively, the processor may include one or more processors configured in tandem via a bus to enable independent execution of instructions, pipelining, and/or multithreading. The use of the term "processing circuitry" may be understood to include a single core processor, a multi-core processor, multiple processors internal to the device 200 and controller, and/or remote or "cloud" processors.

In an example embodiment, the processor 202 may be configured to execute instructions stored in the memory 204 or otherwise accessible to the processor 202. Alternatively, or additionally, the processor 202 may be configured to execute hard-coded functionality. As such, whether configured by hardware or by a combination of hardware with software, the processor 202 may represent an entity (e.g., physically embodied in circuitry) capable of performing operations according to an embodiment of the present disclosure while configured accordingly. Alternatively, as another example, when the processor 202 is embodied as an executor of software instructions, the instructions may specifically configure the processor 202 to perform the algorithms and/or operations described herein when the instructions are executed.

The device 200 and controller further include input/output circuitry 206 that may, in turn, be in communication with processor 202 to provide output to a user and to receive input from a user, user device, or another source. In this regard, the input/output circuitry 206 may comprise a display that may be manipulated by a user or a mobile application. In some embodiments, the input/output circuitry 206 may also include additional functionality such as a keyboard, a mouse, a joystick, a touch screen, touch areas, soft keys, a microphone, a speaker, or other input/output mechanisms. The processor 202 and/or user interface circuitry comprising the processor 202 may be configured to control one or more functions of a display through computer program instructions (e.g., software and/or firmware) stored on a memory accessible to the processor (e.g., memory 204, and/or the like).

The communications circuitry 208 may be any means such as a device or circuitry embodied in either hardware or a combination of hardware and software that is configured to receive and/or transmit data from/to a network and/or any other device, circuitry, or module in communication with the device 200 and controller. In this regard, the communications circuitry 208 may include, for example, a network interface for enabling communications with a wired or wireless communication network. For example, the communications circuitry 208 may include one or more network interface cards, antennae, buses, switches, routers, modems, and supporting hardware and/or software, or any other device suitable for enabling communications via a network. Additionally, or alternatively, the communication interface may include the circuitry for interacting with the antenna(s) to cause transmission of signals via the antenna(s) or to handle receipt of signals received via the antenna(s). These signals may be transmitted by the device 200 and controller using any of a number of wireless personal area network (PAN) technologies, such as Bluetooth® v1.0 through v3.0, Bluetooth Low Energy (BLE), infrared wireless (e.g., IrDA), ultra-wideband (UWB), induction wireless transmission, 3G, 4G, 5G, or the like. In addition, it should be understood that these signals may be transmitted using Wi-Fi, Near Field Communications (NFC), Worldwide Interoperability for Microwave Access (WiMAX) or other proximity-based communications protocols.

The scanning circuitry 210 includes hardware components designed to generate scanning data representative of the physical form of an object 100. In some instances, the scanning circuitry 210 may further be configured to generate a 3D rendering of the object based upon the scanning data and/or analyze the scanning data to determine a position of the device 200 relative to the object 100. The scanning circuitry 210 may utilize processing circuitry, such as the processor 202, to perform its corresponding operations, and may utilize memory 204 to store collected information.

The agent output circuitry 212 includes hardware components designed to determine and/or monitor the output of the sanitizing agent during operation of the scanning device 203. In some instances, the agent output circuitry 212 may further be configured receive an intensity distribution of the sanitizing agent from the sanitizing element 205, compare the intensity distribution with an exposure threshold, and determine an area of the object 100 failing to receive sufficient contact with the sanitizing agent. The agent output circuitry 212 may utilize processing circuitry, such as the processor 202, to perform its corresponding operations, and may utilize memory 204 to store collected information.

In addition, computer program instructions and/or other types of code may be loaded onto a computer, processor or other programmable device circuitry to produce a machine, such that the computer, processor other programmable circuitry that execute the code on the machine create the means for implementing the various functions, including those described in connection with the components of device 200 and associated controller.

As described above and as will be appreciated based on this disclosure, embodiments of the present disclosure may be configured as systems, methods, mobile devices, and the like. Accordingly, embodiments may comprise various means including entirely of hardware or any combination of software with hardware. Furthermore, embodiments may take the form of a computer program product comprising instructions stored on at least one non-transitory computer-readable storage medium (e.g., computer software stored on a hardware device). Any suitable computer-readable storage medium may be utilized including non-transitory hard disks, CD-ROMs, flash memory, optical storage devices, or magnetic storage devices.

Example Operations

Figure 3:
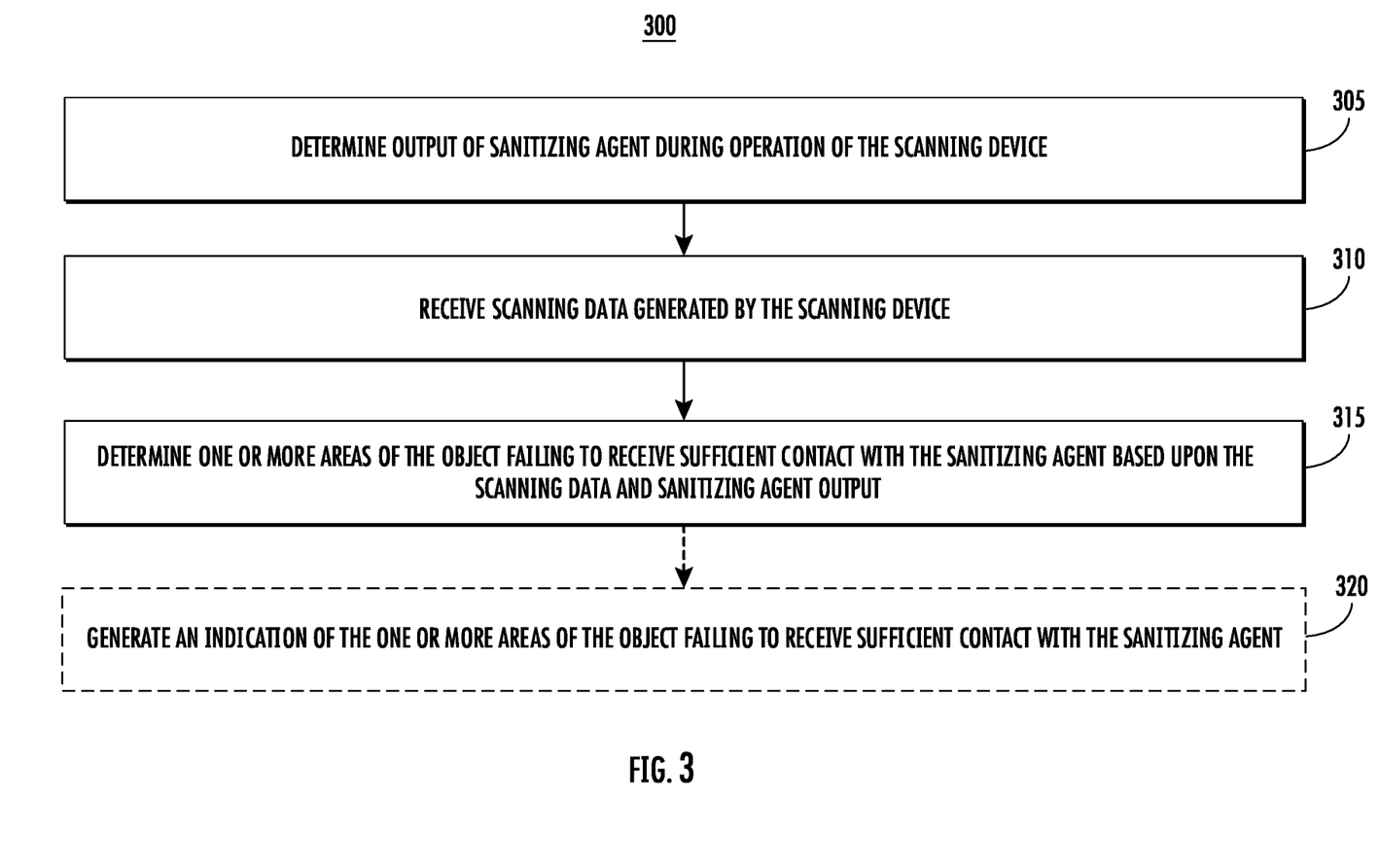
FIG. 3 illustrates an example flowchart for improved sanitization, in accordance with some example embodiments described herein.

FIG. 3 illustrates a flowchart containing a series of operations for improved sanitization in accordance with some example embodiments described herein. The operations illustrated in FIG. 3 may, for example, be performed by, with the assistance of, and/or under the control of the controller of the device 200 (e.g., device for improved sanitization), as described above. In this regard, performance of the operations may invoke one or more of processor 202, memory 204, input/output circuitry 206, communications circuitry 208, scanning circuitry 210, and/or agent output circuitry 212.

As shown in operation 305, the device 200 includes means, such as input/output circuitry 206, communications circuitry 208, agent output circuitry 212, or the like, for determining the output of sanitizing agent by the sanitizing element 205 during operation of the scanning device 203. As described above, the sanitizing element 205 may, for example, include a UV light, lamp, LED, or the like such that the sanitizing agent is UV electromagnetic radiation. As described hereafter with reference to operation 310, a user operating the device 200 may move the device 200 about the object 100 as part of scanning the object 100. Said differently, a user may move the device 200 about the object 100 in order to gather sufficient data (e.g., scanning data) related to the object 100 such that the device 200 may generate a 3D rendering of the object 100. During this operation, the sanitizing element 205 may continuously or intermittently operate to output the sanitizing agent.

By way of continued example, the sanitizing element 205 may be powered or otherwise turned on such that the UV lamp (e.g., sanitizing element 205) outputs UV electromagnetic radiation (e.g., sanitizing agent). In some embodiments, as is evident by the description regarding the scanning data hereafter, this determination by the device 200 (e.g., the controller or equivalent computing device) may correspond to active monitoring of the output of the sanitizing agent. For example, the controller of the device 200 may iteratively receive data from the sanitizing element 205 indicating the current output of sanitizing agent. This output may, in an instance in which the sanitizing element 205 is a UV lamp, correspond to the intensity of the UV electromagnetic radiation fluctuation in the x, y, and z directions (e.g., intensity distribution). Said differently, the device 200 (e.g., via the controller) may determine the variable intensity by actively monitoring the output of the UV electromagnetic radiation in every direction relative to the device 200 over the operating time (e.g., each sanitizing output data entry may be associated with a corresponding time stamp or time data) of the device 200. When used in conjunction with the positional data (e.g., scanning data) as described hereafter, the device 200 (e.g., controller) may be able to associate the output of the sanitizing element 205 with a corresponding position of the device 200.

In other embodiments, this determination by the device 200 (e.g., the controller or equivalent computing device) may correspond to receiving output of the sanitizing agent from one or more prior operations of the device 200 or known characteristics (e.g., average sanitizing agent output) of the sanitizing element 205. For example, the controller of the device 200 may store output data from the sanitizing element 205 (e.g., in memory 204 or the like) indicating the output of sanitizing agent during a prior operation of the device 200 or may query the server 102 to received output data of the sanitizing element 205. This output may, in an instance in which the sanitizing element 205 is a UV lamp, correspond to the intensity of the UV electromagnetic radiation fluctuation in the x, y, and z directions (e.g., intensity distribution).

Thereafter, as shown in operation 310, the device 200 includes means, such as communications circuitry 208, scanning circuitry 210, or the like, for receiving scanning data generated by the scanning device 203. As described above, a user may operate the device 200 by moving the device 200 and associated scanning device 203 about the object 100. The one or more sensors, cameras, or the like of the scanning device 203 may be configured to generate scanning data indicative of the physical form of the object 100. By way of example, in an instance in which the scanning device 203 is a 3D scanner, the one or more 3D cameras of the scanner may generate scanning data at each position relative to the object 100. This scanning data may indicate the relative position of the device 200 (e.g., the x, y, and z coordinates of the device 200) as well as a plurality of 3D data points for rendering the object 100 as a 3D object. Said differently, the scanning device 203 may generate a plurality of scanning data entries that may be used to generate a 3D point cloud or mesh. As the number of scanning data entries increases and the diversity of the entries increases (e.g. the location relative to the object 100 changes), the scanning device 203 may improve the 3D rendering of the object 100. As described above, this positional data may also be time stamped (e.g., time data) and subsequently be paired with the output of the sanitizing agent received at operation 305. In this way, the device 200 may determine the output of sanitizing agent by the sanitizing element 205 at every position relative to the object 100.

Thereafter, as shown in operation 315, the device 200 includes means, such as communications circuitry 208, scanning circuitry 210, or the like, for determining one or more areas of the object 100 failing to receive sufficient contact with the sanitizing agent based upon the scanning data and sanitizing agent output. As described hereafter with reference to FIG. 4, the device 200 analyzing the scanning data of the scanning device 203 in conjunction with an output of the sanitizing agent to determine an intensity distribution of the sanitizing agent at each position relative to the object 100. These intensity distributions may then be compared to one or more exposure thresholds to determine if the object is subjected to sufficient sanitizing agent to disinfect that corresponding portion of the object 100 (e.g., the portion of the object 100 that corresponds to the position of the device 200 or is in the aligned direction of the scanning direction of the scanning device 203 and the output of the sanitizing agent). In embodiments in which the device 200 is configured to cure one or more resins, the exposure thresholds may refer to sufficient sanitizing agent (e.g., UV light) to cure the resin.

By way of continued example, the object 100 may include a plurality of surfaces having various depths or distances from the device 200. Similarly, the user operating the device 200 may fluctuate the distance between the device 200 and the object 100 (e.g., move the device 200 closer and farther from the object 100). As such the one or more exposure thresholds may define an amount of time during which the surface of the object 100 must be subjected to contact with the sanitizing agent of the sanitizing element 205 based upon the position of the device 200 relative to the object 100. Said differently, in instances in which the device 200 is substantially close to the surface of the object 100, the exposure threshold may define a time that is substantially less than the exposure threshold in instance in which the device is substantially far away from the object. Similarly, objects 100 having complex geometries may require additional contact with the sanitizing agent in order to satisfy the exposure threshold. As described hereafter with reference to FIG. 4, the device 200 (e.g., the controller) may compare the intensity distribution for each position of the device 200 relative to the object 100 in order to determine one or more areas of the object 100 failing to receive sufficient contact with the sanitizing agent.

In some embodiments, as shown in operation 320, the device 200 includes means, such as communications circuitry 208, input/output circuitry 206, or the like, for generating an indication of the one or more areas of the object 100 failing to receive sufficient contact with the sanitizing agent. In some embodiments, the device 200 may generate a text notification or other audio/visual que to a user indicating areas of the object 100 that require additional contact with the sanitizing agent. In instances in which a user, system administrator, server 102, or the like has associated a name with the areas of the object 100 (e.g., handle, tabletop, bottom surface, etc.), the indication may refer to these names in the notification to the user.

Figure 5:
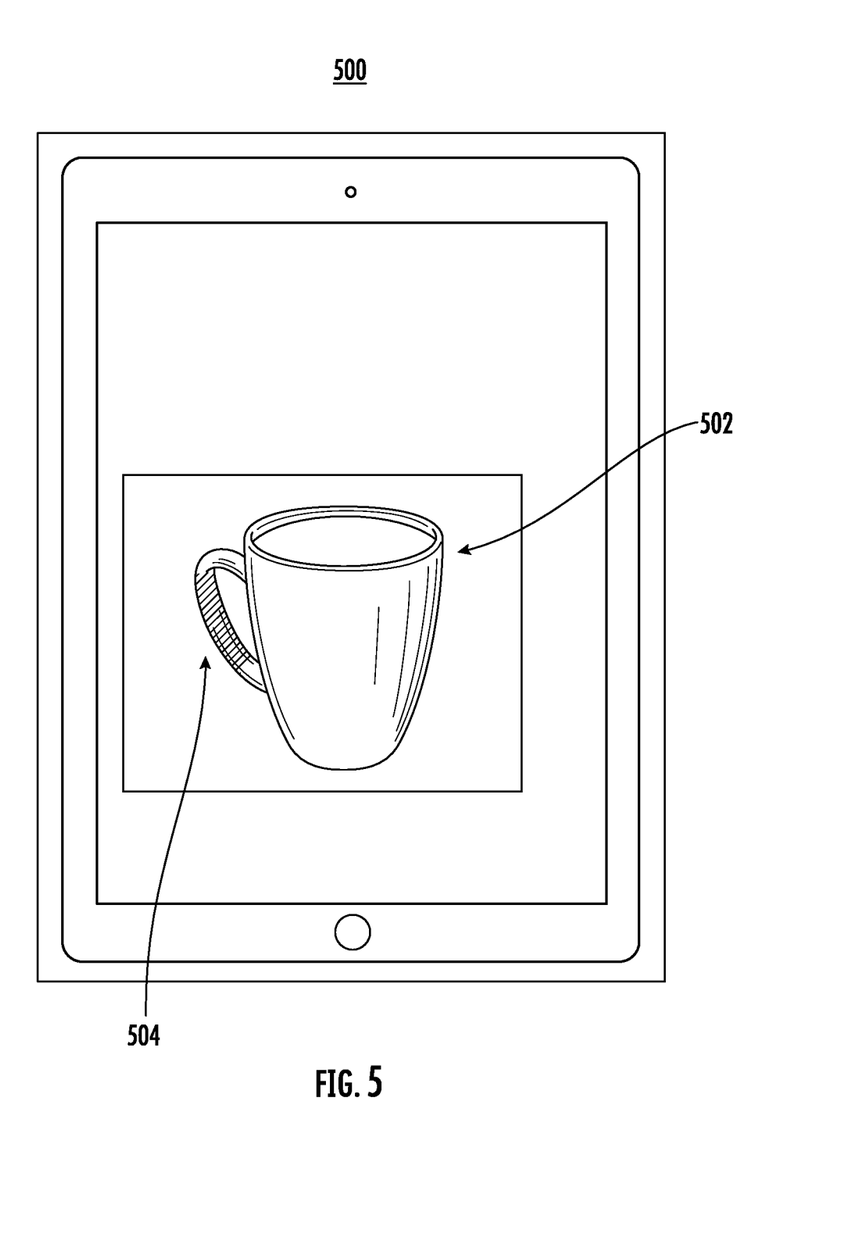
FIG. 5 illustrates an example output rendering, in accordance with some example embodiments described herein.

As described above, in some embodiments, the scanning device 203 may include a 3D scanner configured to, based upon the generated scanning data, generate a 3D rendering of the object 100. In such an embodiment, the indication of the one or more areas of the object 100 failing to receive sufficient contact with the sanitizing agent may be shown on the 3D rendering of the object 100. As illustrated in FIG. 5, for example, the handle of a cup (e.g., object 100) may be shown in a different color in order to indicate that the colored area requires additional contact with the sanitizing agent. In other embodiments, the area that do not require additional contact with the sanitizing agent (e.g., areas that satisfy the exposure threshold) may also be colored (e.g., in a color, shading, grading, etc.) that differs from the coloring used to indicate the areas that require additional contact.

Figure 4:
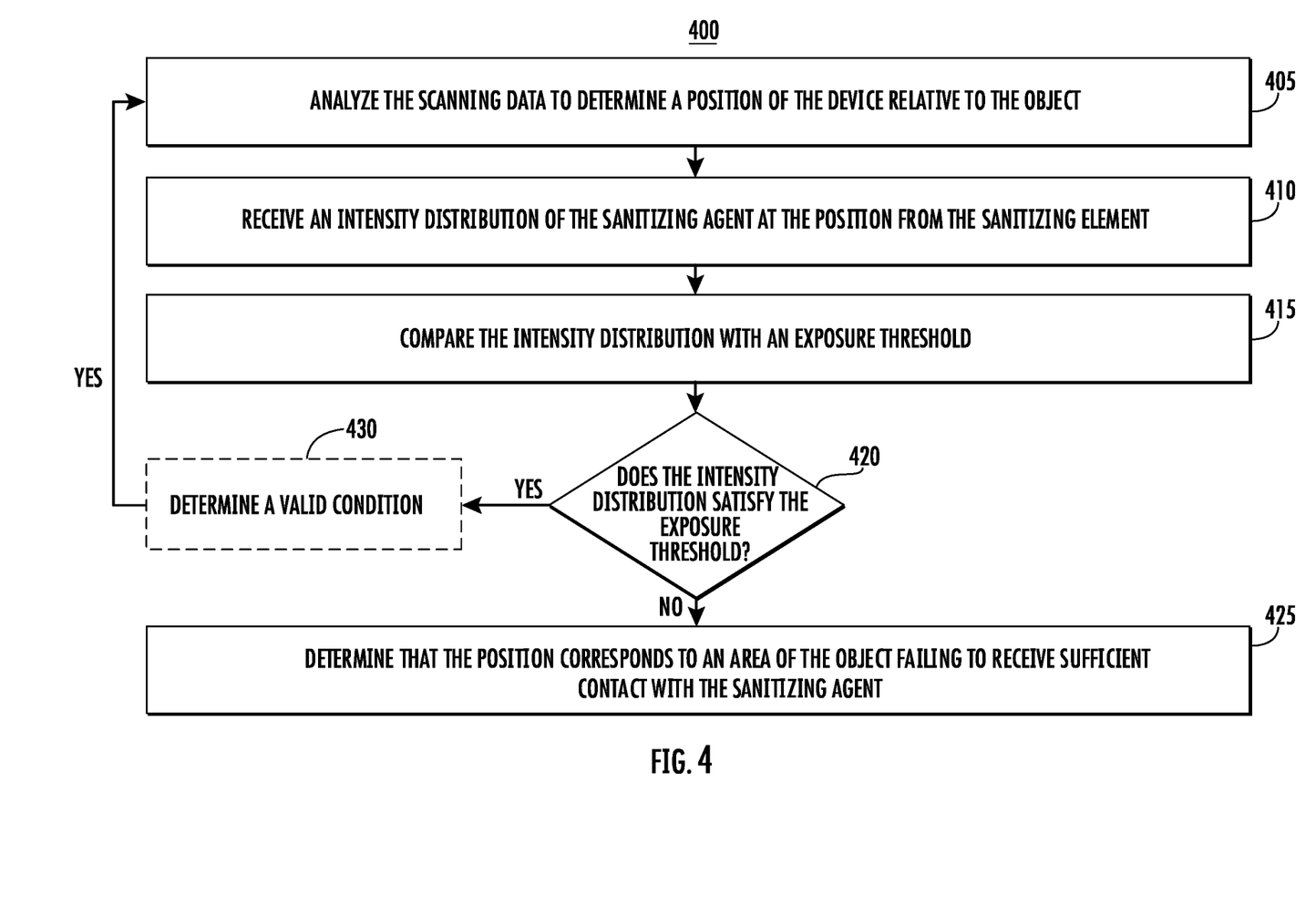
FIG. 4 illustrates an example flowchart for intensity distribution analysis, in accordance with some example embodiments described herein.

Turning next to FIG. 4, a flowchart is shown for intensity distribution analysis in accordance with some example embodiments described herein. The operations illustrated in FIG. 4 may, for example, be performed by, with the assistance of, and/or under the control of the controller of the device 200 (e.g., device for improved sanitization), as described above. In this regard, performance of the operations may invoke one or more of processor 202, memory 204, input/output circuitry 206, communications circuitry 208, scanning circuitry 210, and/or agent output circuitry 212.

As shown in operation 405, the device 200 includes means, such as input/output circuitry 206, communications circuitry 208, scanning circuitry 210, or the like, for analyzing the scanning data to determine a position of the device 200 relative to the object 100. As described above, in an instance in which the scanning device 203 is a 3D scanner, the one or more 3D cameras of the scanner may generate scanning data at each position relative to the object 100. This scanning data may be indicative of the relative position of the device 200 (e.g., the x, y, and z coordinates of the device 200) and may be generated via any 3D imaging technique including time-of-flight, triangulation, conoscopic holography, structured light, modulated light, volumetric, and/or any contact, non-contact active, or non-contact passive technique. As the user moves the device 200 about the object 100, scanning data is generated for each position at which the device 200 is located. As the number of scanning data entries increases, the accuracy of the position determines may increase. Additionally, each of these scanning data entries may be time stamped (e.g., time data) so as to associate the position of the device 200 with the corresponding intensity distribution of the sanitizing element 205 at the position (e.g., associated the intensity distribution at a particular time with scanning data received at the same time).

As shown in operation 410, the device 200 includes means, such as input/output circuitry 206, communications circuitry 208, agent output circuitry 212, or the like, for receiving an intensity distribution of the sanitizing agent at the position from the sanitizing element 205. As described above, the device 200 (e.g., the controller or equivalent computing device) may iteratively receive data from the sanitizing element 205 indicating the current output of sanitizing agent. In some embodiments, however, receiving the intensity distribution of the sanitizing agent may refer to receiving output of the sanitizing agent from one or more prior operations of the device 200 or known characteristics (e.g., average sanitizing agent output) of the sanitizing element 205. This output may, in an instance in which the sanitizing element 205 is a UV lamp, correspond to the intensity of the UV electromagnetic radiation fluctuation in the x, y, and z directions (e.g., intensity distribution). Said differently, the device 200 at operation 410 may monitor the variable intensity (e.g., intensity distribution) of the output of the UV electromagnetic radiation in every direction relative to the device 200 over the operating time. Similar to the scanning data at operation 405, each of these intensity distribution entries may be time stamped (e.g., time data) so as to associate the intensity distribution of the sanitizing element 205 with position of the device 200 (e.g., associate the intensity distribution at a particular time with scanning data received at the same time). In doing so, the intensity distribution at each position relative to the object 100 (e.g., the associated areas of the object 100 in the scanning direction of the device 200) may be determined.

As described herein, the intensity distribution of the sanitizing agent may correspond to the intensity of the UV electromagnetic radiation fluctuation in the x, y, and z directions (e.g., intensity distribution). This distribution, however, may fluctuate during operation of the device 200 due to external factors (e.g., the material of the object 100, ambient UV light, etc.) as well as due to the nature of the electromagnetic radiation (e.g. flux or the like). As such, the device 200 may be configured to determine and/or monitor the intensity distribution of the sanitizing element 205 during operation in order to ensure appropriate and consistent output of the sanitizing agent. In this way, the device 200 may operate to manage the output of a complex sanitizing agent to ensure a valid condition (e.g., disinfected object, cured resin, etc.) of the object 100.

As shown in operations 415 and 420, the device 200 includes means, such as input/output circuitry 206, communications circuitry 208, agent output circuitry 212, scanning circuitry 210, or the like, for comparing the intensity distribution with an exposure threshold. As described above, the object 100 may include a plurality of surfaces having various depths or distances from the device 200. Similarly, the user operating the device 200 may fluctuate the distance between the device 200 and the object 100 (e.g., move the device 200 closer and farther from the object 100). As such, the exposure threshold may define an amount of time during which the surface of the object 100 must be subjected to contact with the sanitizing agent of the sanitizing element 205 based upon the position of the device 200 relative to the object 100. Therefore, the exposure threshold comparison at operations 415, 420 may include an exposure threshold associated with the particular position of the device (e.g., determined at operation 405). For example, the exposure threshold may define an intensity distribution (measure in milliwatts per square centimeter ($mW/cm^2$), millijoules per square centimeter ($mJ/cm^2$), or the like) at a particular distance from the object 100, and for a particular amount of time. For example, the exposure threshold may be 1.0 $mW/cm^2$ for a time period of five (5) seconds at a distance of fifteen (15) cm from the object 100. Although described with reference to these particular values herein, the present disclosure contemplates that the minimum intensity distribution, time, and distance may be varied by the device 200 based upon the intended application.

In some embodiments, if any of the elements of the exposure threshold (e.g., intensity distribution, time, and/or distance) are not satisfied by the intensity distribution at operations 415, 420, the device 200 (e.g. controller) may determine that the intensity distribution fails to satisfy the exposure threshold. By way of example, a user operating the device 200 may move the device relative to the object 100 during operation such that a distance component of the exposure threshold is not satisfied. However, the user may well exceed the time component of the exposure threshold such that the surface of the object receives sufficient contact with the sanitizing agent. In an abundance of caution, however, the device 200 may determine that the position corresponds to an area of the object 100 failing to receive sufficient contact with the sanitizing agent at operation 425. In other embodiments, the exposure threshold may dynamically adjust during operation to account for movement of the device 200 relative to the object 100. Thereafter, as shown in operation 425, the device 200 includes means, such as communications circuitry 208, scanning circuitry 210, or the like, for determining one or more areas of the object 100 failing to receive sufficient contact with the sanitizing agent as described above with reference to operation 315.

As described above, the intensity distribution of the sanitizing agent may fluctuate during operation of the device 200. Similarly, the exposure threshold utilized by the device 200 may be configured to dynamically change during operation of the device. Said differently, the device 200 may determine a change in the intensity distribution of the sanitizing agent output while a user moves the device 200 about the object 100. In response, the controller of the device 200 may dynamically modify, augment, or adjust the exposure thresholds to accommodate changes to the intensity distribution In some embodiments, operations 415, 420 may be performed in real-time during operation of the device 200 (e.g., movement around the object 100). By way of example, the device 200 may perform the comparisons between the intensity distribution and the associated exposure threshold for each position as the user is positioning the device 200 at said position. In other embodiments, however, the device 200 may await completion of the user operation (e.g., once the device 200 has received sufficient scanning data to generate a 3D rendering of the object 100) before performing operations 415, 420. Said differently, the device 200 may allow the 3D rendering of the object 100 to complete such that the area(s) of the object failing to receive sufficient contact with the sanitizing agent may be determined based upon a complete collection of scanning data so as to reduce potential errors associated with partially complete renderings (e.g. insufficient positional data).

In some embodiments, as shown in operation 430, the device 200 includes means, such as communications circuitry 208, scanning circuitry 210, agent output circuitry 212, or the like, for determining a valid condition in an instance in which the intensity distribution at each position of the object 100 satisfies the exposure threshold(s). By way of example, a user operating the device 200 may direct and position the device 200 at each surface of the object 100 for a sufficient amount of time at a sufficient intensity distribution so as to satisfy the exposure threshold for each position relative to the object 100. In such an instance, the device 200 may determine a valid condition for the object (e.g., the object 100 is sanitized) and may store the determination of the valid condition for the object 100. The device 200 may transmit data to the server 102 via the network 104 indicating the determination of the valid condition for the object and the server 102 may store this data. In some embodiments, the memory 204 of the device 200 may store this determination. By way of example, a hospital environment may, by policy, governmental regulation, professional code, etc., require that objects within the environment be sanitized or disinfected after use or after a defined period of time. By storing determinations of a valid condition, the device 200 may operate to provide a verifiable record of sanitization operations.

Furthermore, in some embodiments, the device 200 (e.g., controller) may be configured to modify the exposure threshold based upon one or more previous determinations of the valid condition for the object 100. In particular, prior iterations of sanitization operations performed by the device 200 for the object 100 may be used to refine the intensity distribution, distance, and/or time components of the exposure thresholds. In some embodiments, the geometry, size, and/or shape of the object 100 may be such that some portions or areas of the object 100 require additional contact with the sanitizing agent. By way of example, the object 100, in a disinfecting application, may include any number of surfaces, nooks, crevices, cavities, and/or openings that require additional contact with the sanitizing agent in order to ensure proper disinfection of the object 100. Similarly, in a resin curing embodiment, the object 100 may include surfaces, nooks, crevices, cavities, and/or openings that require additional contact with the sanitizing agent in order to ensure proper curing of the resin applied to the object 100.

In some embodiments, the material of the object 100 may further operate to determine the required contact with the sanitizing agent. By way of example, the device 200 may be moved about an object 100 formed of various materials (e.g., cardboard, fabric, adhesives, tapes, plastics, polymers, ceramics, and/or the like) such that sufficient contact with the sanitizing agent for each material varies. Similarly, the exposure threshold for each material of the object 100 may also vary. As described above, the minimum intensity distribution, time, and distance of the exposure threshold may thus be varied in response to the determined materials of the object 100.

In some embodiments, as described above, the device 200 may determine a valid condition for the object (e.g., the object 100 is sanitized or cured) and may store the determination of the valid condition for the object 100. The device 200 may transmit data to the server 102 via the network 104 indicating the determination of the valid condition for the object and the server 102 may store this data. In some embodiments, the memory 204 of the device 200 may store this determination. These one or more prior determinations of a valid condition of the object may further be used by the device 200 to generate a trainable model and/or labeled data set. In particular, various machine learning techniques may be employed by the device 200 to improve further operations of the device 200. For example, the trainable model and/or labeled data set may be used to improve the 3D modeling of the scanning device 203, the determination of the areas of the object 100, modifications to the exposure thresholds, and/or the like.

Alternatively or additionally, the device 200 may employ one or more image recognition and mapping techniques in the course of performing the operations described herein. For example, the device 200 may generate data (e.g., scanning data) representative of the physical form of the object 100 in conjunction with data regarding the sanitizing element 205 (e.g., intensity distribution or the like). Based upon this data, the device 200 may generate trainable models and/or labeled data sets that may be accessed by the device 200 in further operations in response to images captured by the device 200. Said differently, the device 200 may capture images of the object 100 during operation, and these images may be analyzed by the device 200 (or other computing device in communication with the device 200) to identify prior operations of the device 200 with objects having similar geometries and/or materials to the current object. In this way, the device 200 may operate to modify the exposure thresholds to improve further operations of the device 200.

FIGS. 3-4 thus illustrate flowcharts describing the operation of apparatuses, methods, and computer program products according to example embodiments contemplated herein. It will be understood that each flowchart block, and combinations of flowchart blocks, may be implemented by various means, such as hardware, firmware, processor, circuitry, and/or other devices associated with execution of software including one or more computer program instructions. For example, one or more of the operations described above may be implemented by an apparatus executing computer program instructions. In this regard, the computer program instructions may be stored by a memory 204 of device 200 and executed by a processor 202 of device 200. As will be appreciated, any such computer program instructions may be loaded onto a computer or other programmable apparatus (e.g., hardware) to produce a machine, such that the resulting computer or other programmable apparatus implements the functions specified in the flowchart blocks. These computer program instructions may also be stored in a computer-readable memory that may direct a computer or other programmable apparatus to function in a particular manner, such that the instructions stored in the computer-readable memory produce an article of manufacture, the execution of which implements the functions specified in the flowchart blocks. The computer program instructions may also be loaded onto a computer or other programmable apparatus to cause a series of operations to be performed on the computer or other programmable apparatus to produce a computer-implemented process such that the instructions executed on the computer or other programmable apparatus provide operations for implementing the functions specified in the flowchart blocks.

The flowchart blocks support combinations of means for performing the specified functions and combinations of operations for performing the specified functions. It will be understood that one or more blocks of the flowcharts, and combinations of blocks in the flowcharts, can be implemented by special purpose hardware-based computer systems which perform the specified functions, or combinations of special purpose hardware with computer instructions.

With reference to FIG. 5, an example output rendering 500 is illustrated. As shown, the indication generated at, for example, operation 320 may include a 3D rendering 502 of the object 100. The 3D rendering 502 may further including a signal 504 indicating an area of the object failing to receive sufficient contact with the sanitizing agent. As shown, the handle (e.g., signal) of the cup (e.g., object 100) as rendered 502 is highlighted so as to indicate that further contact with the sanitizing agent is necessary. All though illustrated in FIG. 5 with a highlighted signal, the present disclosure contemplates that any indicator may be used to alert a user that a particular area of the object requires additional contact with the sanitizing agent.

CONCLUSION

Many modifications and other embodiments set forth herein will come to mind to one skilled in the art to which this disclosure pertain having the benefit of the teachings presented in the foregoing descriptions and the associated drawings. Therefore, it is to be understood that this disclosure is not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A device for improved sanitization, the device comprising:
a sanitizing device configured to output a sanitizing agent;
a scanning device configured to generate scanning data of a physical form of an object;
a housing supporting the sanitizing device and the scanning device, wherein the housing is configured to position the sanitizing device proximate to the scanning device such that a scanning direction of the scanning device substantially aligns with the output of the sanitizing agent; and
a controller operatively coupled to the sanitizing device and the scanning device, the controller configured to:
determine the output of the sanitizing agent during operation of the scanning device;
receive the scanning data generated by the scanning device;
determine one or more areas of the object failing to receive sufficient contact with the sanitizing agent based upon the scanning data and sanitizing agent output in an instance in which an intensity distribution of the sanitizing agent fails to satisfy an exposure threshold; and
determine a valid condition in an instance in which the intensity distribution of the sanitizing agent at each position of the object satisfies the exposure threshold.

2. The device according to claim 1, wherein the sanitizing device comprises an ultraviolet (UV) light such that the sanitizing agent comprises UV electromagnetic radiation.

3. The device according to claim 1, wherein the scanning device comprises a three dimensional (3D) scanner.

4. The device according to claim 1, wherein the controller is further configured to generate an indication of the one or more areas of the object failing to receive sufficient contact with the sanitizing agent.

5. The device according to claim 1, wherein the controller is further configured to, in response to receiving the scanning data, generate a three dimensional (3D) rendering of the object.

6. The device according to claim 5, wherein the controller is further configured to generate an indication of the one or more areas of the object failing to receive sufficient contact with the sanitizing agent on the 3D rendering of the object.

7. The device according to claim 1, wherein the controller is further configured to:
analyze the scanning data to determine a position of the device relative to the object;
receive the intensity distribution of the sanitizing agent at the position from the sanitizing device;
compare the intensity distribution with the exposure threshold; and
determine that the position corresponds to the one or more area of the object failing to receive sufficient contact with the sanitizing agent.

8. The device according to claim 7, wherein the scanning data further comprises associated time data.

9. The device according to claim 1, wherein the controller is further configured to store the determination of the valid condition for the object.

10. The device according to claim 1, wherein the controller is further configured to modify the exposure threshold based upon one or more previous determinations of the valid condition.

11. A computer-implemented method for improved sanitization, the computer-implemented method comprising:
receiving scanning data generated by a scanning device, wherein the scanning data is associated with a physical form of an object;
determining an output of a sanitizing agent from a sanitizing device during operation of the scanning device, wherein the sanitizing device is positioned proximate to the scanning device such that a scanning direction of the scanning device substantially aligns with the output of the sanitizing agent; and
determining one or more areas of the object failing to receive sufficient contact with the sanitizing agent based upon the scanning data and sanitizing agent output in an instance in which an intensity distribution of the sanitizing agent fails to satisfy an exposure threshold; and
determining a valid condition in an instance in which the intensity distribution of the sanitizing agent at each position of the object satisfies the exposure threshold.

12. The computer-implemented method according to claim 11, further comprising generate an indication of the one or more areas of the object failing to receive sufficient contact with the sanitizing agent.

13. The computer-implemented method according to claim 11, further comprising:

analyzing the scanning data to determine a position of the device relative to the object;

receiving the intensity distribution of the sanitizing agent at the position from the sanitizing device;

comparing the intensity distribution with the exposure threshold; and determining that the position corresponds to the one or more area of the object failing to receive sufficient contact with the sanitizing agent.

14. The computer-implemented method according to claim 11, further comprising storing the determination of the valid condition for the object.

15. The computer-implemented method according to claim 11, further comprising modifying the exposure threshold based upon one or more previous determinations of the valid condition.

16. A computer program product comprising at least one non-transitory computer-readable storage medium having computer-readable program code portions stored therein, the computer-readable program code portions comprising an executable portion configured to:

receive scanning data generated by a scanning device associated with a physical form of an object;

determine an output of a sanitizing agent from a sanitizing device during operation of the scanning device, wherein the sanitizing device is positioned proximate to the scanning device such that a scanning direction of the scanning device substantially aligns with the output of the sanitizing agent; and determine one or more areas of the object failing to receive sufficient contact with the sanitizing agent based upon the scanning data and sanitizing agent output in an instance in which an intensity distribution of the sanitizing agent fails to satisfy an exposure threshold; and determine a valid condition in an instance in which the intensity distribution of the sanitizing agent at each position of the object satisfies the exposure threshold.

17. The computer program product according to claim 16, wherein the computer-readable program code portions comprising the executable portion are configured to:

analyze the scanning data to determine a position of the device relative to the object;

receive the intensity distribution of the sanitizing agent at the position from the sanitizing device;

compare the intensity distribution with the exposure threshold; and determine that the position corresponds to the one or more area of the object failing to receive sufficient contact with the sanitizing agent.

* * * * *